United States Patent [19]

Jackson

[11] 4,146,493

[45] Mar. 27, 1979

[54] DIELECTRIC FLUID

[75] Inventor: Larry L. Jackson, Midland, Mich.

[73] Assignee: The Dow Chemical Company, Midland, Mich.

[21] Appl. No.: 571,894

[22] Filed: Apr. 25, 1975

Related U.S. Application Data

[63] Continuation-in-part of Ser. No. 377,839, Jul. 9, 1973, abandoned.

[51] Int. Cl.² .............................................. H01B 3/18
[52] U.S. Cl. ...................................................... 252/65
[58] Field of Search .......................................... 282/65

[56] References Cited

U.S. PATENT DOCUMENTS 2,170,989   8/1939   Coleman et al. ........................ 252/65

OTHER PUBLICATIONS

Clark, Insulating Materials for Design and Engineering Practice, pp. 206–207.

*Primary Examiner*—John D. Welsh

[57] ABSTRACT

Dielectric fluids having good electrical properties, low viscosities, low vapor pressures, low freezing points, high flash points and excellent biodegradability comprise a mixture of an alkylhalodiphenyl oxide and a chloro- or bromodiphenyl oxide.

11 Claims, No Drawings

DIELECTRIC FLUID

CROSS-REFERENCE TO RELATED APPLICATIONS

This application is a continuation-in-part of my earlier application Ser. No. 377,839 filed July 9, 1973, now abandoned.

BACKGROUND OF THE INVENTION

The most widely used dielectric fluids heretofore have been highly chlorinated hydrocarbons, such as the polychlorinated biphenyls (PCB's). While these are functionally satisfactory, they are highly objectionable from an environmental and ecological standpoint because of their high toxicity and extreme resistance to biodegradation. For this reason, acceptable substitutes have been actively sought.

Polyhalogenated diphenyl oxides are known to be useful as dielectric fluids, either alone (U.S. Pat. No. 2,022,634) or in admixture with alkyldiphenyl oxides (U.S. Pat. No. 2,169,995). Such fluids are no longer acceptable, however, because the polyhalo component is not sufficiently biodegradable.

Alkylated diphenyl oxides have been recommended for use as dielectric fluids (U.S. Pat. No. 2,170,809) but have never found wide use because of their poor electrical properties, especially their low dielectric constants.

Lower alkylchlorodiphenyl oxides are known and have been suggested for use as dielectric fluids (U.S. Pat. No. 2,170,989) but have not been accepted in the industry because of high volatility, low flash point and relatively poor electrical properties.

SUMMARY OF THE INVENTION

Dielectric fluids having suitable physical, chemical, electrical and biological properties comprise a mixture of diphenyl oxide (DPO) compounds, at least one of which is an alkylhalo DPO and at least one is a monohalo DPO. The alkylhalo DPO has 1–3 alkyl groups of about 2–12 carbon atoms each, the total alkyl carbon content being about 2–16, and one halogen substituent. In another embodiment, the alkylhalo DPO has 1–2 alkyl groups of about 4–12 carbon atoms each, the total alkyl carbon content being about 4–16, and one halogen substituent. The halogen in both components of the fluid is chlorine or bromine. In one embodiment, the proportions of halo DPO and alkylhalo DPO are between about 30:70 and 70:30; i.e., the mixture should contain at least about 30% by weight of each component. The preferred proportions are about 50:50.

DETAILED DESCRIPTION OF THE INVENTION

In its broadest aspect, the dielectric fluid of the invention comprises a mixture of (a) at least one monochloro- or monobromodiphenyl oxide and (b) at least one monochloro- or monobromoalkyldiphenyl oxide having 1–3 alkyl groups, each of which has 2–12 carbon atoms, said oxide having a total of about 2–16 alkyl carbon atoms. In another embodiment, (a) and (b) are each present in the mixture in an amount between about 5 and about 95 weight percent based upon the total weight of the mixture.

As indicated above, the monochloro- and monobromoalkyldiphenyl oxide component in the mixture can have 1 to 3 alkyl substituents. Thus, for example, in a specific embodiment, the dielectric fluid can comprise a mixture of (a) monochlorodiphenyl oxide and (b) a mixture of monochlorobutyldiphenyl oxide, monochlorodibutyldiphenyl oxide, and monochlorotributyldiphenyl oxide. In a more specific embodiment, in the mixture defined above, the monochlorodiphenyl oxide is present in an amount between about 5 and about 40 weight percent, the monochlorobutyldiphenyl oxide is present in an amount between about 30 and about 80 weight percent, the monochlorodibutyldiphenyl oxide is present in an amount between about 10 and about 50 weight percent, and the monochlorotributyldiphenyl oxide is present in an amount between about 2 and about 10 weight percent.

The alkylation and halogenation of DPO are well known in the art. It is recognized in the art that these reactions inherently produce a mixture of isomeric, homologous and/or analogous compounds wherein the number and arrangement of the substituents vary. Such mixtures, usually referred to as cogeneric mixtures, can be partially or completely resolved by fractional distillation and/or crystallization, or by other known means. For the present purpose, however, it has been found that such separation is not ordinarily necessary, provided the average values stay within the limits set forth herein. In particular, polyhalo components should not be present in more than very low concentrations because of their increased toxicity and resistance to biodegradability. For most applications, concentrations of dihalo compounds of up to about 5% can be tolerated.

SPECIFIC EMBODIMENTS OF THE INVENTION

Examples 1–11

The table below shows several important properties of some typical examples of the invention.

In the table the DPO compounds are identified by the substituents on the DPO nucleus. Thus, for instance, $Cl-C_{12}-$ is monochlorododecyldiphenyl oxide. The hexyl and butyl substituents are represented by $C_6$ and $C_4$, respectively. Except as indicated, the mixtures used in the examples were 50:50 by weight.

TABLE I

| Ex. No. | DPO Cpds. | Flash Pt., °F. | Fire Pt., °F. | Pour Pt., °C. | Boiling Pt., °C. | Dielectric Const. | Dissipation Factor $10^3$ HZ | Dissipation Factor $10^4$ HZ |
|---|---|---|---|---|---|---|---|---|
|   | Cl— | 290 | 340 | −27 | 271 | 4.7 | 0.003 |   |
|   | Br— | 350 | 530 | −40 | 305 | 4.3 | .003 |   |
|   | Cl—$C_{12}$— | 450 | 480 | 0 | >400 | 3.9 | .0001 |   |
| 1 | Cl—$C_{12}$ / Cl | 325 | 370 | −37 | >300 | 4.3 | .002 |   |
| 2 | Cl—$C_{12}$— / Br | 360 | 470 | −29 | 350 | 4.2 | .003 |   |
|   | Cl—$C_6$— | 390 | 415 | −30 | 340 | 4.3 |   | .0002 |
| 3 | Cl—$C_6$— / Cl— | 315 | 345 | −27 | 290 | 4.4 |   | .0002 |

TABLE I-continued

| Ex. No. | DPO Cpds. | Flash Pt., °F. | Fire Pt., °F. | Pour Pt., °C. | Boiling Pt., °C. | Dielectric Const. | Dissipation Factor $10^3$ HZ | Dissipation Factor $10^4$ HZ |
|---|---|---|---|---|---|---|---|---|
| 4 | Cl—C$_6$— | 360 | 440 | −35 | 310 | 4.3 | | .0003 |
|   | Br— Cl—C$_4$— | 335 | 375 | <−40 | 310 | 4.5 | | .0002 |
| 5 | Cl—C$_4$— | | | | | | | |
|   | Cl— | 300 | 335 | <−40 | 280 | 4.7 | | .0002 |
| 6 | Cl—C$_4$— | | | | | | | |
|   | Br— | 340 | 385 | <−40 | 305 | 4.5 | | .0002 |
| 7(a) | Cl—C$_{12}$ | 310 | 340 | <−20 | 270-460 | 4.6 | | 0.0002 |
|   | Cl | | | | | | | |
| 8(b) | Cl—C$_{12}$ | 355 | 385 | <−20 | 270-460 | 4.2 | | 0.0002 |
|   | Cl | | | | | | | |
| 9(c) | Cl—C$_3$ | 330 | 370 | <−45 | — | 4.6 | | 0.0002 |
|   | Cl | | | | | | | |
| 10(d) | Cl—C$_4$ | 350 | 375 | <−45 | 290-410 | 4.5 | | 0.0001 |
|   | Cl | | | | | | | |
| 11(e) | Cl—C$_6$ | 340 | 360 | <−45 | 300-410 | 4.3 | | 0.0001 |
|   | Cl | | | | | | | |

(a) 70% by weight Cl DPO and 30% by weight Cl—C$_{12}$
(b) 70% by weight Cl—C$_{12}$ and 30% by weight Cl DPO
(c) 79% by weight Cl—C$_3$ and 21% by weight Cl DPO
(d) 83% by weight Cl—C$_4$ and 17% by weight Cl DPO
(e) 64% by weight Cl—C$_6$ and 36% by weight Cl DPO All of the above materials are readily biodegradable, as are the homologous mono- and dialkylchloro- and -bromo-DPO compounds.

Example 12

The toxicity to fish of the dielectric fluids was determined by a 96 hour static water test using Fathead minnows. In these runs, the toxicity of monochlorodiphenyl oxide, monochlorobutyldiphenyl oxide, and mixtures thereof was determined. Table II below sets forth the results which were obtained. Ten fish were employed in each run. The LC$_{50}$ is defined as the concentration of the oxides in the water in milligrams per liter at which 50 percent or five of the fish remain unaffected (the five remaining fish were either dead or demonstrated evidence of toxicity).

TABLE II

| | | | | | | | | |
|---|---|---|---|---|---|---|---|---|
| Wt. % C$_4$Cl—DPO | 0 | 70 | 75 | 80 | 85 | 90 | 95 | 100 |
| Wt. % Cl—DPO | 100 | 30 | 25 | 20 | 15 | 10 | 5 | 0 |
| LC$_{50}$ Expected | | | 5.7 | 6.8 | 8.5 | 11 | 17 | 34 |
| LC$_{50}$ Observed | 1.7 | 7 | 7 | 7 | 20 | 27 | NT | NT |

NT means not toxic at the solubility in water

As can be seen from the data in Table II, the EC$_{50}$ for the monochlorodiphenyl oxide by itself is only 1.7 mg/liter of water. The presence of the monochloroalkyldiphenyl oxide apparently diminishes the toxicity of the Cl DPO because the actual EC$_{50}$ is much greater than expected for mixtures containing up to 15 percent Cl DPO.

Other alkylhalo DPO compounds that may be mixed with Cl-DPO and/or Br-DPO, in proportions of 30-70% for example, to produce dielectric fluids according to the invention include the ethyl-, propyl-, hexyl-, octyl-, decyl-, dihexyl-, dioctyl-, hexyl octyl-, heptyl nonyl-, and hexyl decyl-Cl-DPO and the corresponding alkyl-Br-DPO compounds. In these compounds, the positions of the substituents on the DPO nucleus is of little significance in the present invention. Likewise, the configuration of the alkyl groups is relatively unimportant, though those having a high degree of branching are less readily biodegradable than those having straight chains.

I claim:

1. A dielectric fluid comprising at least about 30% by weight of each of
    (a) at least one monochloro- or monobromodiphenyl oxide and
    (b) at least one monochloro- or monobromoalkyldiphenyl oxide having 1-2 alkyl groups, each of which has about 4-12 carbon atoms, said oxide having a total of about 4-16 alkyl carbon atoms.

2. The fluid of claim 1 wherein (a) is monochlorodiphenyl oxide.

3. The fluid of claim 1 wherein (a) is monobromodiphenyl oxide.

4. The fluid of claim 1 wherein (b) is dodecylmonochlorodiphenyl oxide.

5. The fluid of claim 4 wherein (a) and (b) are present in a ratio of about 50:50 by weight.

6. The fluid of claim 5 wherein (a) is monochlorodiphenyl oxide.

7. The fluid of claim 6 wherein (b) is dodecylmonochlorodiphenyl oxide.

8. A dielectric fluid comprising a mixture of
    (a) at least about 5 weight percent of at least one monochloro- or monobromodiphenyl oxide and
    (b) at least about 30 weight percent of at least one monochloro- or monobromoalkyldiphenyl oxide having 1-3 alkyl groups, each of which has about 2-12 carbon atoms, said oxide having a total of about 2-16 alkyl carbon atoms.

9. The fluid of claim 8 wherein (a) is present in an amount between about 5 and about 40 weight percent and (b) is present in an amount of at least about 30 weight percent.

10. The fluid of claim 8 wherein (a) is monochlorodiphenyl oxide and (b) is a mixture of monochlorobutyldiphenyl oxide, monochlorodibutyldiphenyl oxide, and monochlorotributyldiphenyl oxide.

11. The fluid of claim 10 wherein the monochlorodiphenyl oxide is present in an amount between about 5 and about 40 weight percent, the monochlorobutyldiphenyl oxide is present in an amount between about 30 and about 80 weight percent, the monochlorodibutyldiphenyl oxide is present in an amount between about 10 and about 50 weight percent, and the monochlorotributyldiphenyl oxide is present in an amount between about 2 and about 10 weight percent.

* * * * *